United States Patent [19]

Traber et al.

[11] Patent Number: 5,438,144
[45] Date of Patent: Aug. 1, 1995

[54] USE OF 1,4-DIHYDROPYRIDINES IN DIABETES

[75] Inventors: Jörg Traber, Lohmar, Germany; Willem H. Gispen, Bilthoven, Netherlands

[73] Assignee: Troponwerke GmbH & Co. KG, Cologne, Germany

[21] Appl. No.: 90,224

[22] Filed: Jul. 9, 1993

Related U.S. Application Data

[63] Continuation-in-part of Ser. No. 917,552, Jul. 21, 1992, abandoned.

[30] Foreign Application Priority Data

Jul. 30, 1991 [DE] Germany ............ 41 25 116.4

[51] Int. Cl.⁶ .......................................... C07D 211/22
[52] U.S. Cl. .................... 546/321; 544/356; 544/866
[58] Field of Search ............... 514/356, 866; 546/321

[56] References Cited

U.S. PATENT DOCUMENTS

| | | | |
|---|---|---|---|
| 3,485,847 | 12/1969 | Bossert et al. | 260/295.5 |
| 3,932,645 | 1/1976 | Meyer et al. | |
| 4,406,906 | 9/1983 | Meyer et al. | |
| 4,994,476 | 2/1991 | Poindexter | 546/321 |

OTHER PUBLICATIONS

Robertson et al. Chem Abst 118: 139526z.
P. A. Steen et al., "Nimodipine Improves Outcome when Given After . . . ", Anesthesiology, 62, 406–414 (not 411) (1985).
E. Sporel-Özakat et la., "Nimodipine and Central Nervous System Function: New Vistas", Schattauer Verlag Stuttgart, 71–85 (1989).
R. E. Sporel-O zakat, Dissertation, "Peripheral Nerve Damage and Repair: A Pharmacological Therapeutical Approach", University of Utrecht, 1990, pp. 93–98.
A. K. Sharma et al., "Animal Models: Pathology and Pathophysiology", Diabetic neruopathy (1987), pp. 237–252.
Y. Harati, "Diabetic Peripheral Neuropathies", Ann. Intern. Med. 107 (1987) pp. 546–559.
A. C. Kappelle et al., "The Ca-antagonist nimodipine counteracts the onset . . . ", Neuroscience Research Communications, vol. 10, No. 2, 1992, pp. 95–104.
M. Welsch et al., "Nimodipin wirk neuroprotekiv ohne Steingerung . . . ", Pharmazeutische Zeitung Wissenschaft, vol. 135, 1990, pp. 29–34.
C. E. E. M. van der Zee et al., "Oral administration of nimodipine accelerates . . . ", Neuroscience Letters, vol. 83, 1987, pp. 143–148.
P. Longhurst, "In vitro contractile responses of vasa deferentia . . . ", J. Auton. Pharmac (1991) vol. 11, pp. 63–71.
Neuroscience Letters, 83 (1987), 143–48, C. E. E. M. van der Zee et al.
Toxicol Appl Pharmacol 111(3) 514–522 1991.
"Futative acurotrophic factors in the protection of platin-induced peripheral nativepathy in fats" Biological Abstracts 13(5) A8–10,

*Primary Examiner*—Peter O'Sullivan
*Attorney, Agent, or Firm*—Sprung Horn Kramer & Woods

[57] ABSTRACT

The invention relates to the use of 1,4-dihydropyridines having calcium antagonistic action, in particular of nimodipine, for the preparation of medicaments for controlling damage to peripheral nerves which is caused by diabetes.

4 Claims, 2 Drawing Sheets

USE OF 1,4-DIHYDROPYRIDINES IN DIABETES

This is a continuation-in-part of application Ser. No. 917,552, filed Jul. 21, 1992, now abandoned.

The invention relates to the use of 1,4-dihydropyridines having calcium antagonistic action, in particular of nimodipine, for the preparation of medicaments for controlling damage to peripheral nerves which is caused by diabetes.

The dihydropyridines which can be employed according to the invention, their preparation and their use as circulatory and cerebrally active agents have been disclosed (compare German Patent Specification 2,117,571, EPB 4650). For the active compound nimodipine (1,4-dihydro-2,6-dimethyl-4-(3'-nitrophenyl)pyridine 3-β-methoxyethyl ester 5-isopropyl ester), in addition to the cerebral effects such as improvements in memory, learning behaviour and the motor field, certain neuroprotective effects are also known (compare Steen P. A. et al., Anesthesiology, 62, 406–411 (1985)). In addition to these cerebral effects of nimodipine, effects on peripheral nerves are also described. The publication by R. E. Sporel-Özakat et al., Nimodipine and central nervous system function: New Vistas, Schattauer Verlag Stuttgart, 71–85 (1989) describes that, after administration of nimodipine to rats, the peripheral nerves are better protected, in particular with respect to cis-platin neuropathy. In this publication, reference is also made to the fact that the mechanism of action of nimodipine is not known and further investigations regarding this are urgently needed.

The publication of C. E. E. M. van der Zee et al., Neuroscience Letters, 83 (1987) 143–148 describes the positive effect of nimodipine on mechanically damaged peripheral nerves. The prior art contains no indication that 1,4-dihydropyridines having calcium antagonistic action, in particular nimodipine, can be employed in the therapy and prophylaxis of damage to the peripheral nerves which is caused by diabetes.

One of the most frequent types of late damage in diabetes mellitus is peripheral neuropathy. The prevalence rate for this is over 60% of the patients suffering from diabetes mellitus. The symptoms include pains in the extremities, muscle weakness up to paralysis symptoms and diverse dysfunctions of the autonomic nervous system such as diarrhoea or impotence, Owing to this damage caused by diabetes, there is a consistent decrease in the nerve conduction rate of both sensory and motor nerves. This nerve conduction rate is thus a readily measurable parameter for determining this damage.

To date, there is no established method for treating such neuropathies and an urgent need thus exists for a therapeutically active agent.

It has already been attempted to employ aldose reductase inhibitors for this therapy. These substances inhibit the enzyme which catalyses the conversion of glucose to sorbitol. In diabetes mellitus, such a glucose oversupply is present, as a result of which an excess of sorbitol is formed which can lead, for example, to cloudiness of the lens of the eye, and which is regarded as a reason for the neuropathy which is caused by diabetes, Aldose reductase inhibitors have already been clinically tested in this indication. The expectations placed on them, however, have not been fulfilled.

As already indicated above, it is also known for the calcium antagonist nimodipine that it has certain neuroprotective effects. For example, it accelerates the regeneration of the function of peripheral nerves after mechanical lesion. Additionally, it is described that nimodipine in the rat after a specific intoxication with the cytostatic cis-platin antagonises selective disorders of the nerve conduction rate of sensory peripheral nerves. The nerve conduction rate of motor peripheral nerves is not affected by cis-platin.

A corresponding intoxication with acrylamide likewise leads to a reduction of the conduction rate of sensory and motor nerves. It is known that nimodipine does not antagonise this damage to peripheral nerves (compare R. E. Sporel-Özakat, Dissertation, University of Utrecht, 1990, pages 93–98). These results show that the nerve protective action of nimodipine is not of the general type and can thus not be derived from the prior art. The person skilled in the art would not expect that nimodipine has a therapeutic effect on the specific peripheral neuropathy which is induced by diabetes mellitus.

Surprisingly, it has now been found that nimodipine antagonises damage to sensory and motor peripheral nerves which is caused by chronic excess of sugar. This effect occurs both after prophylactic administration and after therapeutic administration. Thus, the person skilled in the art is for the first time able to treat therapeutically peripheral neuropathies which are caused by diabetes mellitus. It was unforeseeable for the person skilled in the art that calcium antagonists of the nimodipine type would have such specific therapeutic effects on peripheral nerves.

The invention relates to the use of calcium antagonists from the 1,4-dihydropyridine family, in particular nitrophenyl substituted dihydropyridines with alkyl ester groups in the 3- and 5-positions, e.g. nifedipine, nisoldipine, nitrendipine and especially nimodipine, for controlling neuropathies which are caused by diabetes mellitus. Of particular importance is the control of those neuropathies which occur in the peripheral nervous system.

The preparation of the active compound nimodipine and the preparation of medicaments containing nimodipine for the treatment of such neuropathies is carried out by customary methods, for example by extending the active compound with solvents and/or excipients and then converting into customary formulations such as tablets, coated tablets, granules, syrups, emulsions, suspensions and solutions using inert, non-toxic pharmaceutically suitable auxiliaries.

Administration is carried out in a customary manner, preferably orally. On oral administration, the dosage is about 0.05 to 20 mg/kg, preferably 0.1 to 10 mg/kg of body weight.

The surprising therapeutic effect of the present invention is confirmed by the following use examples:

In male Wistar rats, the insulin-producing pancreas cells are damaged by a single administration of streptozotocin (50 mg/kg i.v.), which leads to chronically increased glucose levels. In the diabetic rats damaged in this way, the nerve conduction rates are distinctly reduced (compare A. K. Sharma et al., Diabetic neuropathy (1987), 237–252 and Y. Harati, Ann. Intern. Med. 107 (1987) 546–559). The results of the test are to be inferred from the curves of FIGS. 1 to 4. The curves a in each case represent the nerve conduction rate of the control groups, the curves c those in damaged diabetic rats which have received no nimodipine and the curves b the nerve conduction rate in diabetic rats treated with nimodipine. Whereas in the healthy control animals the nerve conduction rate of both sensory (FIGS. 1 and 3, curves a) and motor nerves (FIGS. 2 and 4, curves a) rises continuously over time, the nerve conduction rate in the diabetic animals not treated with nimodipine is virtually unchanged (in each case curves c for sensory nerves in FIGS. 1 and 3, and for motor nerves in FIGS. 2 and 4).

After administration of nimodipine (20 mg/kg i.p. every 48 hours), the disorder induced by the excess of sugar is significantly compensated. This applies both for prophylactic nimodipine treatment (curves b in FIGS. 1 and 2) and for therapeutic nimodipine treatment (curves b in FIGS. 3 and 4).

BRIEF DESCRIPTION OF THE DRAWINGS

FIG. 1: Prophylactic effect of nimodipine on the conduction rate of sensory nerves In each case, the average values ($\pm$SEM) for the conduction rates of sensory nerves (CRSN) 0, 2, 4, 6, 8 and 10 weeks after streptozotocin administration (50 mg/kg i.v.) are shown. Group 1 (curve b, n=11) was treated with nimodipine (20 mg/kg i.p. every 48 h in 1 ml/kg of polyethylene glycol), group 2 (curve c, n=11) only with the solvent (1 ml/kg i.p.). Group 3 (curve a, n=11) is a non-diabetic control group treated neither with streptozotocin nor with nimodipine, but only with 1 ml/kg of polyethylene glycol. All experiments were carried out on male Wistar rats (11-12 weeks old at the start of the experiment).

The statistical analysis showed that in streptozotocin-treated diabetic animals the nimodipine treatment led to a significant increase in the CRSN ($p<0.001$). The CRSN of untreated non-diabetic control animals was significantly higher than that of the solvent- or nimodipine-treated diabetic rats ($p<0.001$).

Figure 1:
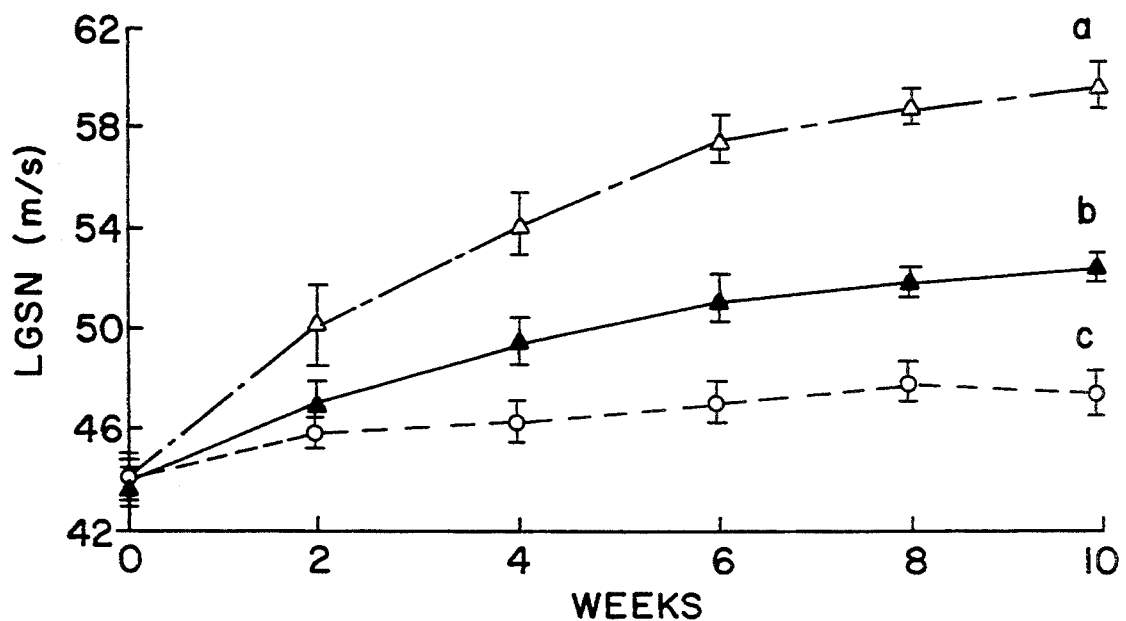
In FIG. 1 there is shown, in graphical form, the prophylactic effect of nimodipine on the conduction rate of sensory nerves.
Figure 2:
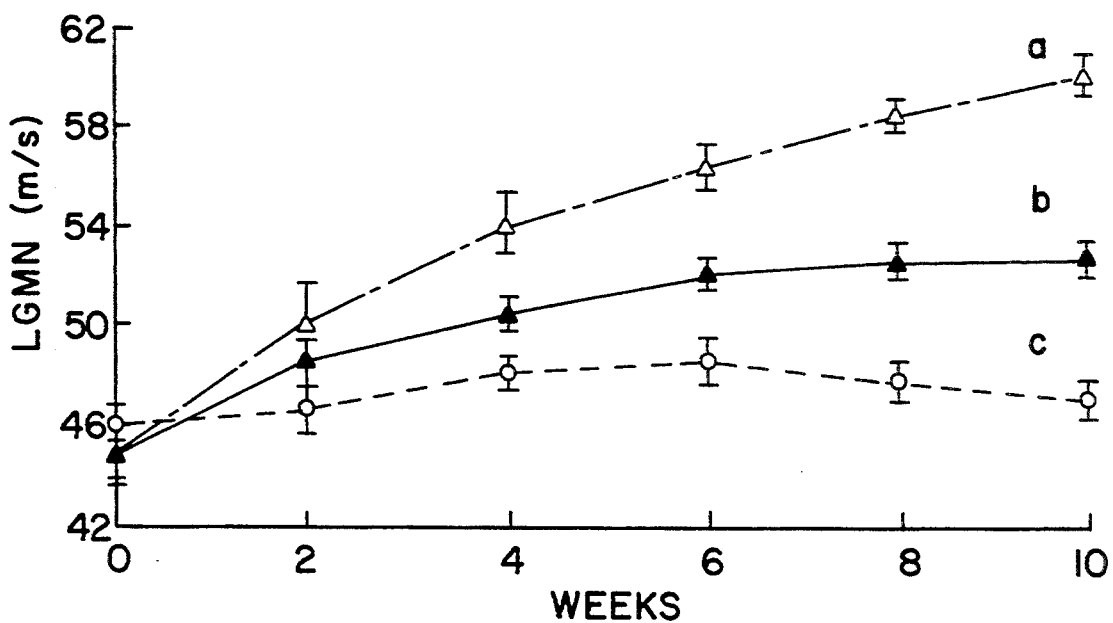
In FIG. 2, there is shown, in graphical form, the prophylactic effect of nimodipine on the conduction rate of motor nerves.

FIG. 2: Prophylactic effect of nimodipine on the conduction rate of motor nerves In each case, the average values ($\pm$SEM) for the conduction rates of motor nerves (CRMN) 0, 2, 4, 6, 8 and 10 weeks after streptozotocin administration (50 mg/kg i.v.) are shown. Group 1 (curve b, n=11) was treated with nimodipine (20 mg/kg i.p. every 48 h in 1 ml/kg of polyethylene glycol), group 2 (curve c, n=11) only with the solvent (1 ml/kg i.p.). Group 3 (curve a, n=11) is a non-diabetic control group treated neither with streptozotocin nor with nimodipine, but only with 1 ml/kg of polyethylene glycol. All experiments were carried out on male Wistar rats (11-12 weeks old at the start of the experiment).

The statistical analysis showed that in streptozotocin-treated diabetic animals the nimodipine treatment led to a significant increase in the CRMN ($p<0.001$). The CRMN of untreated non-diabetic control animals was significantly higher than that of the solvent- or nimodipine-treated diabetic rats ($p<0.001$).

Figure 3:
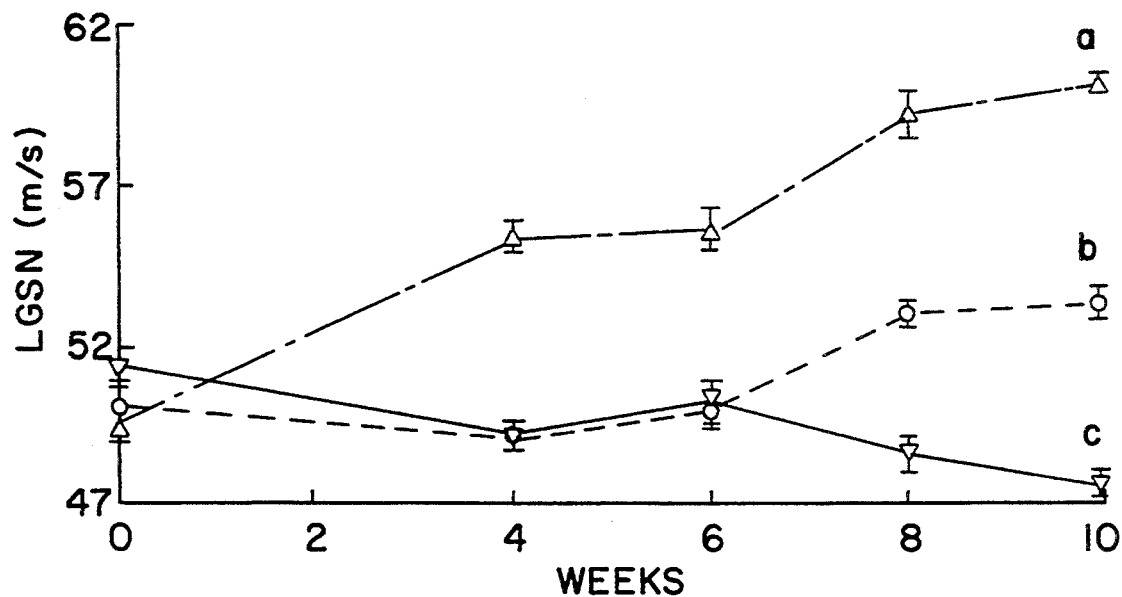
In FIG. 3, there is shown, in graphical form, the therapeutic effect of nimodipine on the conduction rate of sensory nerves.

FIG. 3: Therapeutic effect of nimodipine on the conduction rate of sensory nerves In each case, the average values ($\pm$SEM) for the conduction rates of sensory nerves (CRSN) 0, 4, 6, 8 and 10 weeks after streptozotocin administration (50 mg/kg i.v.) are shown. Group 1 (curve b, n=12) was treated with nimodipine (20 mg/kg i.p. every 48 h in i ml/kg of polyethylene glycol), group 2 (curve c, n=12) only with the solvent (1 ml/kg i.p.). The treatment of the diabetic rats with nimodipine or solvent was carried out 4 weeks after the start of streptozotocin administration, a time at which a significant decrease in the CRSN in comparison with non-diabetic control animals not treated with streptozotocin was measurable (group 3, curve a, n=12). All experiments were carried out on male Wistar rats (11-12 weeks old at the start of the experiment). The statistical analysis showed that in streptozotocin-treated diabetic animals the nimodipine treatment led to a significant increase in the CRSN ($p<0.001$). The CRSN of untreated non-diabetic control animals was significantly higher than that of the solvent- or nimodipine-treated diabetic rats ($p<0.001$).

Figure 4:
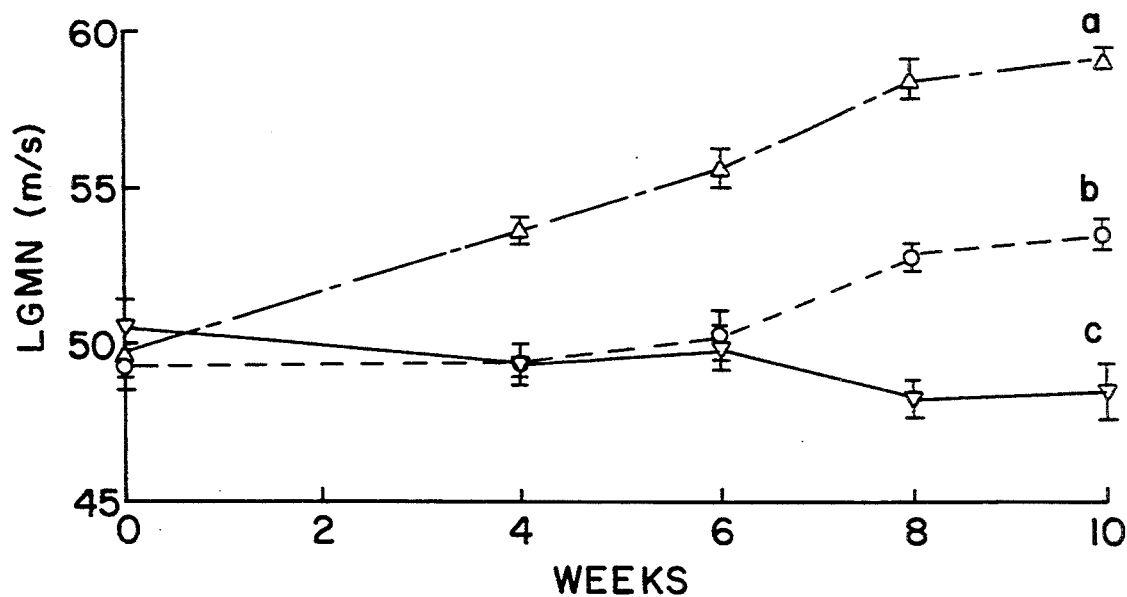
In FIG. 4, there is shown, in graphical form, the therapeutic effect of nimodipine on the conduction rate of motor nerves.

FIG. 4: Therapeutic effect of nimodipine on the conduction rate of motor nerves

In each case, the average values ($\pm$SEM) for the conduction rates of motor nerves (CRMN) 0, 4, 6, 8 and 10 weeks after streptozotocin administration (50 mg/kg i.v.) are shown. Group 1 (curve b, n=12) was treated with nimodipine (20 mg/kg i.p. every 48 h in 1 ml/kg of polyethylene glycol), group 2 (curve c, n=12) only with the solvent (1 ml/kg i.p.). The treatment of the diabetic rats with nimodipine or solvent was carried out 4 weeks after the start of streptozotocin administration, a time at which a significant decrease in the CRMN in comparison with non-diabetic control animals not treated with streptozotocin was measurable (group 3, curve a, n=12). All experiments were carried out male Wistar rats (11-12 weeks old at the start of the experiment).

The statistical analysis showed that in streptozotocin-treated diabetic animals the nimodipine treatment led to a significant increase in the CRMN ($p<0.001$). The CRMN of untreated non-diabetic control animals was significantly higher than that of the solvent- or nimodipine-treated diabetic rats ($p<0.001$).

We claim:

1. A method of controlling neuropathies in patients afflicted with diabetes mellitus which compromises administering to such patient an amount effective therefore of calcium antagonist which is a nitrophenyl substituted 1,4-dihydropyridine with alkyl groups in the 3- and 5- positions provided that said antagonist is not nifedipine.

2. The method according to claim 1, wherein the compound administered is nimodipine.

3. The method according to claim 1, wherein the neuropathies are in the peripheral nervous system of the patient.

4. The method according to claim 1, wherein the neuropathies are in the peripheral nervous system of the patient.

* * * * *

UNITED STATES PATENT AND TRADEMARK OFFICE
CERTIFICATE OF CORRECTION

PATENT NO.   : 5,438,144
DATED        : August 1, 1995
INVENTOR(S)  : Traber, et al.

It is certified that error appears in the above-indentified patent and that said Letters Patent is hereby corrected as shown below:

Col. 4, line 50      Before " patients " insert -- human --

Col. 4, lines 51-53  Delete " therefore " and substitute -- therefor --

Col. 4, line 53      After " of " insert -- a --

Signed and Sealed this

Sixteenth Day of January, 1996

Attest:

BRUCE LEHMAN

Attesting Officer    Commissioner of Patents and Trademarks